(12) United States Patent
Morris

(10) Patent No.: US 10,661,016 B2
(45) Date of Patent: May 26, 2020

(54) HOUSING AND DRUG DELIVERY DEVICE HEREWITH

(71) Applicant: Sanofi, Paris (FR)

(72) Inventor: Anthony Paul Morris, Coventry West Midlands (GB)

(73) Assignee: Sanofi, Paris (FR)

( * ) Notice: Subject to any disclaimer, the term of this patent is extended or adjusted under 35 U.S.C. 154(b) by 41 days.

(21) Appl. No.: 15/515,655

(22) PCT Filed: Oct. 9, 2015

(86) PCT No.: PCT/EP2015/073430
§ 371 (c)(1),
(2) Date: Mar. 30, 2017

(87) PCT Pub. No.: WO2016/055625
PCT Pub. Date: Apr. 14, 2016

(65) Prior Publication Data
US 2017/0296750 A1    Oct. 19, 2017

(30) Foreign Application Priority Data
Oct. 9, 2014   (EP) .................................... 14306592

(51) Int. Cl.
*A61M 5/24* (2006.01)
*A61M 5/315* (2006.01)
(Continued)

(52) U.S. Cl.
CPC ............ *A61M 5/24* (2013.01); *A61M 5/3158* (2013.01); *A61M 5/31536* (2013.01);
(Continued)

(58) Field of Classification Search
CPC ................ A61M 5/24; A61M 5/31541; A61M 5/31543; A61M 5/31535; A61M 5/3158; A61M 2005/2485; A61M 2005/2488; A61M 5/20; A61M 2005/2433; A61M 5/3155

See application file for complete search history.

(56) References Cited

U.S. PATENT DOCUMENTS

2010/0168677 A1    7/2010   Gabriel et al.

FOREIGN PATENT DOCUMENTS

| EP | 0702970 | 3/1996 |
| JP | H08-103495 | 4/1996 |

(Continued)

OTHER PUBLICATIONS

International Search Report and Written Opinion in International Application No. PCT/EP2015/073430, dated Jan. 21, 2016, 13 pages.

(Continued)

*Primary Examiner* — Scott J Medway
(74) *Attorney, Agent, or Firm* — Fish & Richardson P.C.

(57) ABSTRACT

The present disclosure is generally directed to a drug delivery device for selecting and dispensing a number of user variable doses of a medicament and to a housing for such a device. The housing comprises an outer housing with a distal end and a cartridge holder with a proximal end, which, when the cartridge holder is attached to the outer housing, is inserted into the distal end of the outer housing. The outer housing is provided with a first fixture for axially constraining a further component part to the outer housing. When the cartridge holder is attached to the outer housing, the proximal end of the cartridge holder axially extends to the first fixture.

16 Claims, 2 Drawing Sheets

(51) Int. Cl.
*A61M 5/32* (2006.01)
*A61M 5/31* (2006.01)

(52) U.S. Cl.
CPC .... *A61M 5/31541* (2013.01); *A61M 5/31553* (2013.01); *A61M 5/31593* (2013.01); *A61M 5/3202* (2013.01); *A61M 2005/2407* (2013.01); *A61M 2005/2488* (2013.01); *A61M 2005/2492* (2013.01); *A61M 2005/3126* (2013.01); *A61M 2005/3154* (2013.01); *A61M 2205/581* (2013.01); *A61M 2205/582* (2013.01); *A61M 2205/60* (2013.01)

(56) References Cited

FOREIGN PATENT DOCUMENTS

| JP | 2007-502146 | 2/2007 | |
|---|---|---|---|
| JP | 2010-527665 | 8/2010 | |
| JP | 2013-524904 | 6/2013 | |
| JP | 2013-539700 | 10/2013 | |
| WO | WO 2005/018721 | 3/2005 | |
| WO | WO 2008/031235 | 3/2008 | |
| WO | WO 2011/131776 | 10/2011 | |
| WO | WO 2012/041931 | 4/2012 | |
| WO | WO 2012/049144 | 4/2012 | |
| WO | WO 2012/152666 | 11/2012 | |
| WO | WO 2013153011 A1 * | 10/2013 | .............. A61M 5/24 |
| WO | WO 2014/033195 | 3/2014 | |
| WO | WO 2014/056874 | 4/2014 | |
| WO | WO 2014/140820 | 9/2014 | |
| WO | WO 2014/166908 | 10/2014 | |

OTHER PUBLICATIONS

International Preliminary Report on Patentability in international Application No. PCT/EP2015/073430, dated Apr. 11, 2017, 9 pages.

* cited by examiner

HOUSING AND DRUG DELIVERY DEVICE HEREWITH

CROSS-REFERENCE TO RELATED APPLICATIONS

This application is a U.S. national stage application under 35 USC § 371 of International Application No. PCT/EP2015/073430, filed on Oct. 9, 2015, which claims priority to European Patent Application No. 14306592.8 filed on Oct. 9, 2014, the entire contents of which are incorporated herein by reference.

TECHNICAL FIELD

The present disclosure is generally directed to a housing for a drug delivery device and to a drug delivery device for selecting and dispensing a number of user variable doses of a medicament comprising such a housing.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

Unpublished patent application PCT/EP2014/056989 refers to a drug delivery device comprising a dose setting member which is axially constrained to an outer housing such that the dose setting member is rotatable with respect to the outer housing. A cartridge holder is attached to the distal end of the outer housing such that the proximal end of the cartridge holder does not overlap the distal end of the dose setting member.

In some cases, it may be desirable to prevent axial detachment of the dose setting member or any further component part from the outer housing even if an axial force is exerted on the dose setting member or the further component part, e.g. by a spring. Thus, certain aspects of the present provide an improved drug delivery device and a respective housing.

According to certain aspects of the disclosure, a housing for a drug delivery device comprises an outer housing with a distal end and a cartridge holder with a proximal end, which, when the cartridge holder is attached to the outer housing, is inserted into the distal end of the outer housing. The outer housing is provided with a first fixture for axially constraining a further component part, for example a dose setting member, to the outer housing. When the cartridge holder is attached to the outer housing, the proximal end of the cartridge holder preferably axially extends to the first fixture. This includes embodiments, where the proximal end of the cartridge holder axially extends over the first fixture, and embodiments, where the proximal end of the cartridge holder ends, preferably shortly, i.e. less than 5 mm, offset in the distal direction from the first fixture. In other words, the proximal end of the cartridge holder and the further component part are arranged to allow an overlapping of these two component parts. This disables an inward movement or deformation of the further component part, and, thus, prevents detachment of the further component part from the outer housing. The further component part is preferably a dose setting member and/or a display member, like a number sleeve, having markings on its outer surface to display e.g. the set dose.

The proximal end of the cartridge holder may comprise at least one proximally extending protrusion, like a proximally extending finger. When the cartridge holder is attached to the outer housing, the at least one proximally extending protrusion axially extends to the first fixture. In other words, the present disclosure does not require that the whole cartridge holder extends to the first fixture. Rather, it is sufficient (and in some cases preferred) if only a part of the cartridge holder extends towards the first fixture.

The first fixture is preferably suitable for snap engagement with the further component part. For example, the first fixture may comprise a groove or bead located on the inner surface of the outer housing. The groove or bead may extend over the whole circumference of the inner surface of the outer housing or only parts thereof, e.g. forming separate ramps. Preferably, the proximal end of the cartridge holder is located radially inwards of the first fixture, when the cartridge holder is attached to the outer housing. In other words, the further component part may be radially interposed between the cartridge holder and the outer housing.

According to a preferred embodiment of the present disclosure, the housing further comprises a housing insert, which is rotationally and/or axially constrained to the outer housing, preferably at a position axially distal from and/or overlapping with the first fixture. The housing insert may comprise one or more engagement features, like a thread, splines, guiding ribs or grooves and/or a bearing or attachment for a spring. The housing insert may be a separate component part which is permanently or temporarily attached to the outer housing or it may be a one-piece component of the outer housing, like an inner web or flange. Typically, the cartridge holder mainly extends distally from such an insert. However, for interaction with the first fixture and/or a component part attached thereto, it is preferred if the proximal end of the cartridge holder, at least partly, extends through the housing insert. For example, the insert may be attached to the outer housing via radially extending arms having a passage for the proximal end of the cartridge holder between the arms. Alternatively, the insert itself may have at least one passage for the proximal end of the cartridge holder.

As an alternative, the housing may comprise a housing insert, which is rotationally and/or axially constrained to the outer housing and located radially inwards of the first fixture at a position axially overlapping with the first fixture. In a preferred embodiment, a thread for engaging a piston rod is part of the housing, and the insert contains splines for preventing rotation of a drive sleeve. In this embodiment, a number sleeve may have an extended distal rim.

In a preferred embodiment the housing further comprises a second fixture for axially constraining the cartridge holder to the outer housing. The second fixture may be located on the inner surface of the outer housing, e.g. at a position axially distal from the first fixture. In other words, there may be two separate fixtures provided on the inner surface of the outer housing which are axially off-set.

In another preferred embodiment the housing further comprises a separate, third fixture for rotationally constraining the cartridge holder to the outer housing. For example, the third fixture comprises at least one distally extending protrusion of the outer housing having longitudinal splines and a splined portion on the outer surface of the cartridge holder.

In still another preferred embodiment the housing further comprises a separate, fourth fixture for axially and/or rotationally constraining a cap to the outer housing. The cap may be designed to receive the cartridge holder or a part thereof, when the cap is attached to the outer housing. Preferably, the fourth fixture is located on the outer surface of the outer housing, for example at a position axially distal from the first fixture, preferably at the axial position of the first or second fixture. If the fourth fixture is located axially at the same position or in the vicinity of the first or second fixture, forces exerted on the first or second fixture tending to bulge the outer housing may be reacted by the fourth fixture, which may act like a reinforcing material added to the wall thickness of the outer housing. Vice versa, the first or second fixture may act like a reinforcement for the fourth fixture. In addition, the cap on the one hand and the cartridge holder or the further component part on the other hand may mutually react radially directed forces.

A drug delivery device for selecting and dispensing a number of user variable doses of a medicament may comprise a housing, e.g. a housing as defined above, a dose setting element rotatable relative to the outer housing during dose setting and dose dispensing, a drive member coupled to the dose setting member via a clutch, and a piston rod coupled to the outer housing and to the drive member. The dose setting member is preferably axially constrained to the outer housing by a first fixture of the outer housing, for example the first fixture as defined above. The first fixture preferably comprises a groove or bead located on the inner surface of the outer housing and a corresponding bead or groove located on the outer surface of the dose setting member. In other words, a snap engagement is provided for permanently or temporarily attaching the dose setting member to the outer housing. Preferably, this snap engagement is designed such that relative rotation between the dose setting member and the outer housing is allowed, while relative axial movement is prevented.

The dose setting member preferably comprises a portion, e.g. a rim, extending axially distal from the bead or groove of the first fixture. The length of this portion may contribute in preventing unintended detachment of the dose setting member, especially if the dose setting member comprises a recessed groove engaging a bead or protrusion of the first fixture with the distally extending portion of the dose setting member having a larger outer diameter than the recessed groove. For example, the distally extending portion may have a length of 0.5 mm to 20 mm, e.g. about 0.75 mm.

To further strengthen attachment of the dose setting member, the at least a portion of the cartridge holder is located radially inwards of the dose setting member and axially overlapping the dose setting member when the cartridge holder is attached to the outer housing. In other words, the dose setting member is radially interposed between the cartridge holder and the outer housing, such that the cartridge holder blocks inward movement of the dose setting member. Thus, as soon as the cartridge holder is fully attached to the outer housing, axial detachment of the dose setting member from the outer housing is prevented.

In a drug delivery device according to the present disclosure the dose setting member is preferably rotatable relative to the outer housing during dose setting, i.e. increasing or decreasing the dose, and dose dispensing between a minimum dose position and a maximum dose position. The drive member may be rotationally coupled to the dose setting member via a slipping clutch during dose setting and rotationally constrained to the dose setting member during dose dispensing.

The drug delivery device may be a disposable device which is intended to be discarded if the cartridge is empty. As an alternative, the device may be a reusable device requiring resetting, e.g. of a piston rod, when replacing an empty cartridge by a new cartridge. In the latter case, the housing insert may be a reset element which is preferably axially constrained to the dose setting element. In addition, the device may comprise at least one spring acting on the reset element, such that, if the cartridge holder is detached from the outer housing, the reset element is axially moved relative to the outer housing into a position in which the dose setting element is rotationally constrained to the outer housing and the drive member is allowed to rotate relative to the outer housing. In other words, detachment of the cartridge holder from the outer housing may allow an axial movement of the reset element and, preferably, the dose setting element into a resetting position, in which the drive member may be rotated relative to the outer housing and relative to the dose setting member. If the piston rod is coupled to the outer housing and to the drive member, e.g. via a threaded interface with the outer housing and a splined interface with the drive member, resetting of the piston rod requires free rotation of the drive member. Thus, resetting of the drug delivery device may be performed simply by pushing back the piston rod or lead screw after removal of the cartridge holder.

In a further development of this embodiment, the clutch between the dose setting element and the drive member is a slipping clutch with first clutch teeth on the drive member and second clutch teeth on a clutch plate, which is rotationally constrained to the dose setting element during dose setting and dose dispensing. For example, the first and/or second clutch teeth may each be distributed as a ring of teeth, preferably facing in the axial direction. The clutch features and the corresponding clutch features may each comprise a series of teeth, preferably saw-teeth, which are allowed to slip over each other if not pressed against each other too firmly. In other words, the clutch features may be overhauled against the bias of a clutch spring by allowing the sleeve and/or the clutch element to translate axially against the force of the clutch spring. This may result in an oscillating axial movement of the sleeve and/or the clutch element due to continued disengagement and following re-engagement into the next detented position. An audible click may be generated by this re-engagement, and tactile feedback may be given by the change in torque input required.

Preferably, the clutch between the drive member and the dose setting element is a slipping clutch which allows relative rotation between the drive member and the dose setting element in both directions during dose setting for increasing or decreasing a set dose. If the device is a spring driven device, the clutch teeth may be designed to provide a different resistance for overcoming the clutch depending on the direction of the relative rotation. For example, the ramp angle may be shallower resulting in a lower resistance in the dose increasing direction and steeper resulting in a higher resistance in the dose decreasing direction.

According to a preferred embodiment, the drug delivery device is a spring driven device. A drive spring, preferably a torsion spring, may be interposed between the housing and the dose setting element. Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member. The drive spring may be pre-charged, at least partly, and/or may be charged by a user during dose setting.

In another preferred embodiment, the drug delivery device further comprises a gauge element radially interposed between the outer housing and the dose setting element. The gauge element is axially movable relative to the outer housing and in threaded engagement with the dose setting element. The outer housing may comprise at least one aperture and the gauge element may comprise at least one aperture. If the dose setting element is a number sleeve which comprises markings on its outer surface, at least one of the markings is visible through the aperture in the gauge element and the aperture in the outer housing during dose setting and dose dispensing. The term aperture may include a simple opening the outer housing or gauge element or a transparent window or lens. A window in the outer housing may be incorporated using a 'twin-shot' molding technology. For example, the outer housing is molding during a 'first shot' in a translucent material, and the outer cover of the outer housing is molding during a 'second shot' in an opaque material.

The gauge element may be axially guided within the outer housing such that rotation of the dose setting element causes an axial displacement of the gauge element. The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the dose setting element, rotation of the dose setting element causes an axial displacement of the gauge element relative to the dose setting element and relative to the outer housing. The gauge element may have the form of a shield or strip extending in the longitudinal direction of the device. As an alternative, the gauge element may be a sleeve. In an embodiment of the disclosure, the dose setting element is marked with a sequence of numbers or symbols arranged on a helical path. With the dose setting element located radially inwards of the gauge element, this allows that at least one of the numbers or symbols on the dose setting element is visible through the aperture or window. In other words, the gauge element may be used to shield or cover a portion of the dose setting element and to allow view only on a limited portion of the dose setting element. This function may be in addition to the gauge element itself being suitable for identifying or indicating the actually set and/or dispensed dose.

In general, the concept of the gauge element and the dose setting element is applicable for various types of devices with or without a drive spring. In a preferred embodiment, the dose setting element, during dose setting, is adapted to undergo a mere rotational movement within the outer housing and relative to the outer housing. In other words, the dose setting element does not perform a translational movement during dose setting. This prevents that the dose setting element is wound out of the outer housing or that the outer housing has to be prolonged for covering the dose setting element within the outer housing.

The relative movements of the gauge element and the dose setting element may further be used to define the minimum dose position and the maximum dose position. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. For example, the gauge element comprises a minimum dose rotational stop and a maximum dose rotational stop and the dose setting element comprises a minimum dose rotational counter stop and a maximum dose rotational counter stop. Abutment of the respective stop and counter stop blocks further relative movement between the gauge element and the dose setting element. As the dose indicator rotates relative to the gauge element during dose setting and during dose dispensing, these two components are suitable to form a reliable and robust limiter mechanism.

The device may further comprise a dispensing button or trigger. The button is preferably a user operable element located proximally of the drive sleeve and the clutch element. When used in a drug delivery device, the button may extend from the proximal end of the device and, preferably, does not change its axial position during dose setting. The button is preferably coupled to a user operable dose selector and may be releasably coupled to a number sleeve component and/or a stationary housing component. In an alternative embodiment, the button may be part of a dose setting arrangement or may be the dose setting member. The button may be a multi-functional element having in addition to the above features e.g. a clicker feature.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. For example, the last dose protection mechanism comprises a nut member interposed between the drive member and the dose setting element (number sleeve) or any other component which rotates during dose setting and dose dispensing. In a preferred embodiment, the dose setting element rotates during dose setting and during dose dispensing, whereas the drive member only rotates during dose dispensing together with the dose setting element. Thus, in this embodiment, the nut member will only move axially during dose setting and will remain stationary with respect to these components during dose dispensing. Preferably, the nut member is threaded to the drive member and splined to the dose setting member. As an alternative, the nut member may be threaded to the dose setting member and may be splined to the drive member. The nut member may be a full nut or a part thereof, e.g. a half nut.

The injection device may comprise at least one clicker mechanism for generating a tactile and/or audible feedback. A feedback may be generated during dose setting (increasing and/or decreasing a dose), dose dispensing and/or at the end of dose dispensing.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments of the disclosure will now be described with reference to the accompanying drawings, in which.

DETAILED DESCRIPTION

Figure 1:
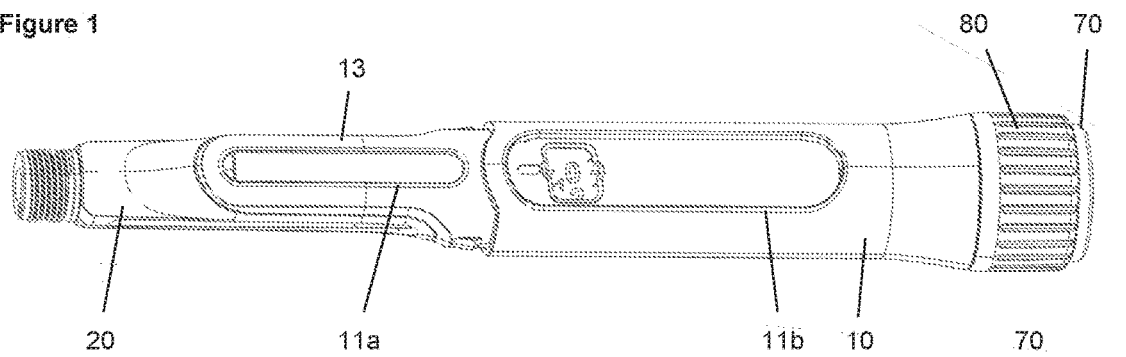
FIG. 1 shows a top view of a drug delivery device according to a first embodiment of the present disclosure.
Figure 2:
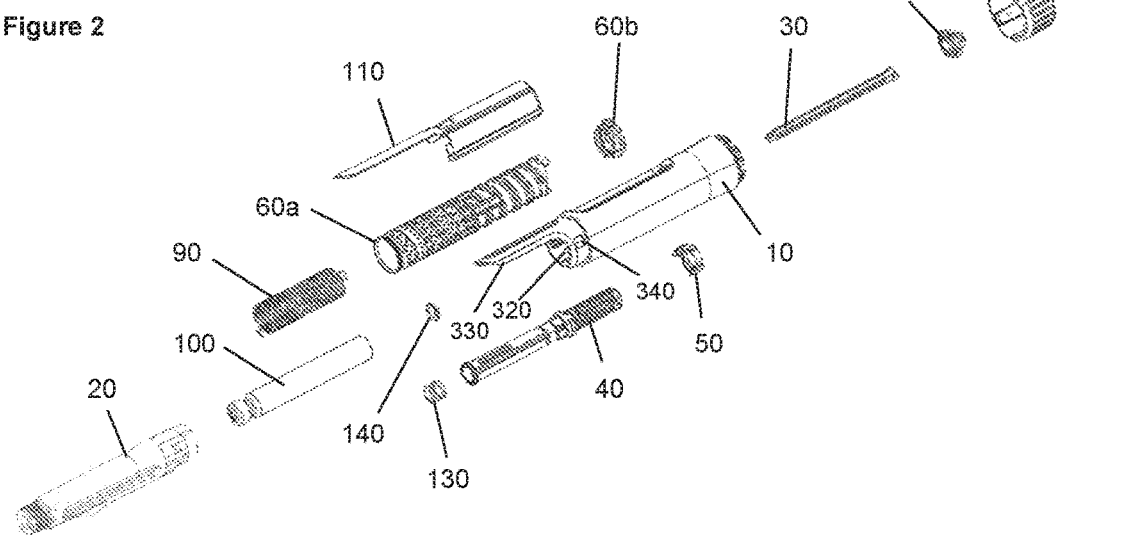
FIG. 2 shows an exploded view of the components of the device of FIG. 1.
Figure 3:
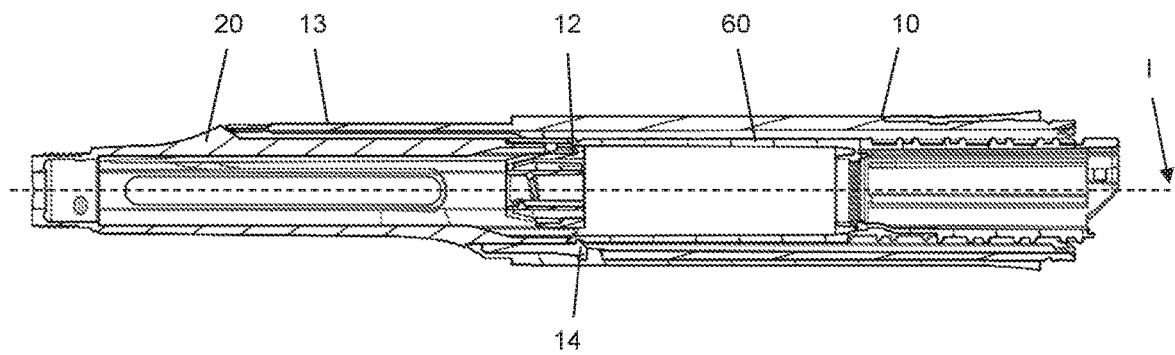
FIG. 3 shows a sectional view of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. An insert 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20.

The Figures depict the housing 10 as a single housing component. However, the housing 10 could comprise two or more housing components which may be permanently attached to each other during assembly of the device. The housing 10 comprises a fixture for engaging number sleeve 60, which fixture has the form of an inner bead 14. The bead 14 is located at a distal region of housing 10 on its inner surface.

Figure 6:
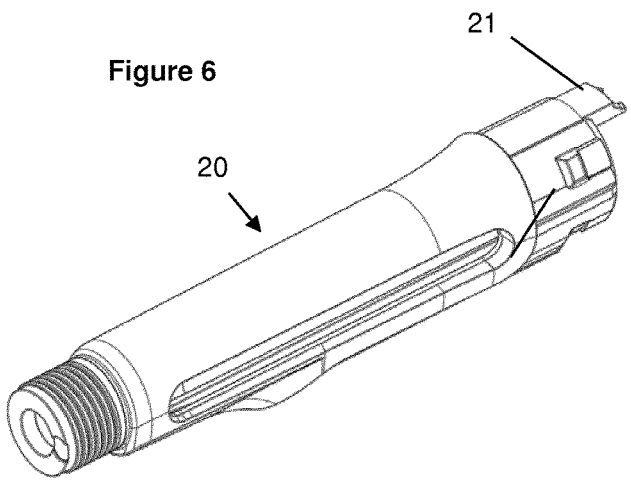
FIG. 6 shows the cartridge holder of the device of FIG. 3.

The cartridge holder 20 is located at the distal side of housing 10 and permanently attached thereto. In some implementations, the housing 10 includes a second fixture 320 configured for axially constraining the cartridge holder 20 to the housing 10. The second fixture 320 can be located on the inner surface of the housing 10. In some implementations, the housing 10 includes a third fixture 330 configured for rotationally constraining the cartridge holder 20 to the housing 10. The third fixture 330 can be, for example, a distally extending protrusion of the housing 10 having longitudinal splines. The cartridge holder 20 may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained on the housing 10. In some implementations, the housing 10 includes a fourth fixture 340 (e.g., one or more clip features) configured for axially and/or rotationally constraining the removable cap to the housing 10. The cartridge holder 20 has an extension 21 in the form of a proximally extending finger (FIG. 6).

The piston rod 30 is rotationally constrained to the drive sleeve 40 via a splined interface. When rotated, the piston rod 30 is forced to move axially relative to the drive sleeve 40, through its threaded interface with the insert 12 of housing 10. The lead screw 30 is an elongate member with an outer thread engaging the corresponding thread of the insert 12 of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined tooth interface with the housing 10 prevents rotation of the drive sleeve 40 during dose setting. This interface comprises a ring of radially extending outer teeth at the distal end of drive sleeve 40 and corresponding radially extending inner teeth of the housing component 10. When the button 70 is pressed, these drive sleeve 40 to housing 10 spline teeth are disengaged allowing the drive sleeve 40 to rotate relative to housing 10. A further splined tooth interface with the number sleeve 60 is not engaged during dialing, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

A further interface of the drive sleeve 40 comprises a ring of ratchet teeth located at the proximal end face of drive sleeve 40 and a ring of corresponding ratchet teeth on the clutch plate 120.

The driver 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline of the driver 40 engages a corresponding track of the lead screw 30.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialing only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament in the cartridge 100.

Figure 5:
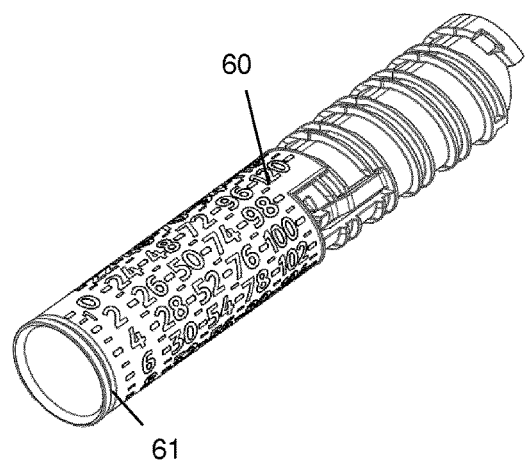
FIG. 5 shows the number sleeve of the device of FIG. 3.

The dose indicator or number sleeve 60 is a tubular element as shown in FIG. 5 in more detail. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons the number sleeve 60 of the embodiment shown in the Figures comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mold tooling and assembly. As an alternative, the number sleeve 60 may be a unitary component. The number sleeve 60 is constrained to the housing 10 by snap engagement to allow rotation but not translation. The number sleeve 60 comprises an annular recess or groove 61 near its distal end which engages a corresponding bead on an inner surface of the housing 10. The number sleeve lower 60a is marked with a sequence of numbers, which are visible through the gauge element 110 and the openings 11a, 11b in the housing 10, to denote the dialed dose of medicament.

Further, the number sleeve lower 60a has a portion with an outer thread engaging the gauge element 110. End stops are provided at the opposite ends of thread to limit relative movement with respect to the gauge element 110.

Clutch features which have the form of a ring of splines are provided inwardly directed on number sleeve upper 60b for engagement with splines of the button 70 during dose setting and dose correction. A clicker arm is provided on the outer surface of number sleeve 60 which interacts with the drive sleeve 40 and the gauge member 110 for generating a feedback signal.

In addition, the number sleeve lower 60a is rotationally constrained to the nut 50 and to the clutch plate 120 via a splined interface comprising at least one longitudinal spline. Further, number sleeve lower 60a comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60b. Thus, it is also splined via splines to the number sleeve upper 60b when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialed. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. The torsion spring 90 is pre-wound upon assembly, such that it applies a torque to the number sleeve 60 when the mechanism is at zero units dialed. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60*a*. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIG. 1, the number sleeve 60 is positioned against its zero dose abutment with the gauge element 110 and the button 70 is not depressed. Dose marking '0' on the number sleeve 60 is visible through the window 11*b* of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges either side of the window area which cover the numbers printed on the number sleeve 60 adjacent to the dialed dose to ensure only the set dose number is made visible to the user.

A specific feature of this disclosure is the inclusion of a visual feedback feature in addition to the discrete dose number display typical on devices of this type. The distal end of the gauge element 110 creates a sliding scale through the small window 11*a* in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting colored component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position.

Figure 4:
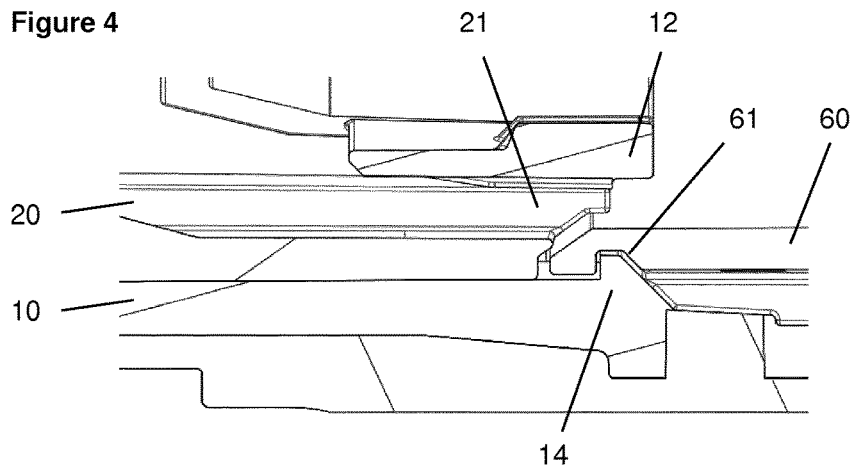
FIG. 4 shows a detail of FIG. 3.

The attachment of cartridge holder 20 to outer housing 10 is now described in more detail with reference to FIGS. 3, 4 and 6. FIG. 3 is illustrated with a simplified representation of the full device. The button 70, dose selector 80, clutch plate 120, last dose nut 50, gauge 110, drive spring 90, piston rod 30, bearing 140, cartridge 100 and clutch spring 130 are not shown.

In the embodiment shown in FIG. 3, the outer housing 10 consists of two parts: a twin-shot molding where the first shot is a translucent material, and the second shot is an opaque material; and the housing insert 12 which is a separate part that becomes rigidly fixed to the outer housing 10 during assembly. As an alternative, the housing insert may be combined with the molding of outer housing 10, or the translucent and opaque sections of the outer housing 10 may be separate components. After assembly of the housing insert 12, the number sleeve 60 is inserted into the outer housing 10 from the proximal end. Its distal end contacts the bead 14, which is a clip feature in the outer housing 10 which forces the distal end of the number sleeve 60 to deflect radially inwards, allowing the bead 14 in the outer housing 10 to engage with the recess 61 near the distal end of the number sleeve.

This clip feature 14, 61 is sufficient to retain the number sleeve 60 during subsequent assembly operations, but the flexibility of the number sleeve 60 may allow it to disengage, e.g. during impact. The proximally extending protrusion 21 on the cartridge holder 20 is used to improve the retention strength (FIG. 4). This protrusion overlaps axially with the end of the number sleeve 60. If the number sleeve 60 deflects radially inwards, it contacts the protrusion 21 on the cartridge holder 20, which in turn contacts the housing insert 12 in the outer housing 10. This limits the allowable deflection, helping to prevent disengagement from the clip in the outer housing 10, and this significantly increases the retention strength of the number sleeve 60 within the outer housing 10.

Figure 7:
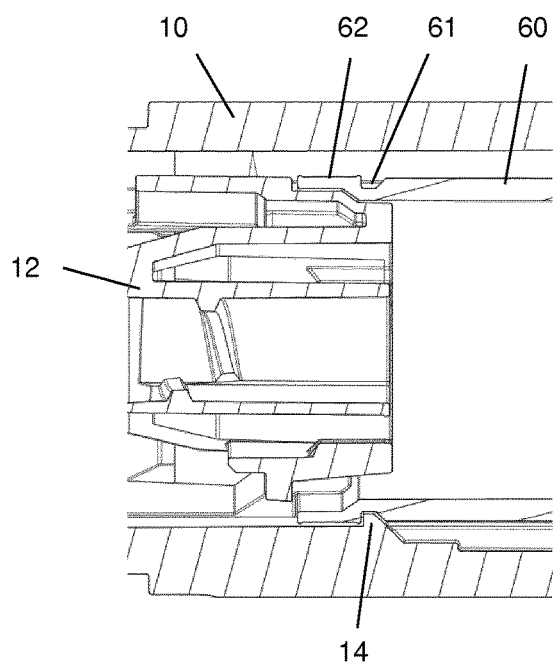
FIG. 7 shows a detail of a drug delivery device according to a further embodiment of the present disclosure.

In an alternative embodiment shown in FIG. 7, the retention strength is increased by extending the number sleeve 60 in the distal direction, rather than extending the cartridge holder 20. In the embodiment of FIG. 7, the number sleeve 60 comprises a rim 62 located distally from recess 61. This provides increased surface area of the number sleeve 60 that may be used for printing.

It is apparent that the feature of increasing retention strength as described above is not limited to devices with a design and function as shown in FIGS. 1 to 3 nor to increase retention strength for a number sleeve. Rather, the cartridge holder 20 may be used to lock any component part, e.g. to the outer housing 10, by engaging a clip attachment from the inside (or even from the outside). In other words, the number sleeve retention features may be included in any pen injector, reducing the likelihood of damage during use and impact.

| Reference Numerals: | |
|---|---|
| 10 | outer housing |
| 11a | opening |
| 11b | opening |
| 12 | insert |
| 13 | strip |
| 14 | bead |
| 20 | cartridge holder |
| 21 | protrusion |
| 30 | piston rod (lead screw) |
| 40 | drive sleeve |
| 50 | nut |
| 60 | dose setting element |
| 60a | number sleeve lower |
| 60b | number sleeve upper |
| 61 | recess |
| 62 | rim |
| 70 | button |
| 80 | dose selector |
| 90 | torsion spring |
| 100 | cartridge |
| 110 | gauge element |
| 120 | clutch plate |
| 130 | clutch spring |
| 140 | bearing |
| l | longitudinal axis |

The invention claimed is:

1. A housing for a drug delivery device, the housing comprising:
an outer housing with a distal end;
a cartridge holder with a proximal end, which, when the cartridge holder is attached to the outer housing, is inserted into the distal end of the outer housing, wherein the outer housing is provided with a first fixture configured to axially constrain a further component part of the drug delivery device to the outer housing to prevent movement of the further component part in a distal direction, wherein, when the cartridge holder is attached to the outer housing, the proximal end of the cartridge holder axially extends to the first fixture and/or overlaps with the further component part;
a second fixture configured to axially constrain the cartridge holder to the outer housing, wherein the second fixture is located on the inner surface of the outer housing at a position axially distal from the first fixture;
a separate third fixture configured to rotationally constrain the cartridge holder to the outer housing; and
a separate fourth fixture configured to axially constrain a cap to the outer housing, wherein the fourth fixture is located on the outer surface of the outer housing at a position axially distal from the first fixture.

2. The housing according to claim 1, wherein the proximal end of the cartridge holder comprises at least one proximally extending protrusion, which, when the cartridge holder is attached to the outer housing, axially extends to the first fixture and/or overlaps with the further component part.

3. The housing according to claim 1, wherein the first fixture comprises a groove or bead located on an inner surface of the outer housing, with the proximal end of the cartridge holder being located radially inwards of the first fixture, when the cartridge holder is attached to the outer housing.

4. The housing according to claim 1, comprising a housing insert rotationally and/or axially constrained to the outer housing at a position axially distal from and/or overlapping with the first fixture, wherein the proximal end of the cartridge holder, at least partly, extends through the housing insert.

5. The housing according to claim 1, comprising a housing insert rotationally and/or axially constrained to the outer housing and located radially inwards of the first fixture at a position axially overlapping with the first fixture.

6. The housing according to claim 1, wherein the third fixture comprises at least one distally extending protrusion of the outer housing having longitudinal splines and a splined portion on an outer surface of the cartridge holder.

7. A drug delivery device for selecting and dispensing a number of user variable doses of a medicament, the device comprising:
a housing, comprising:
an outer housing with a distal end, and
a cartridge holder with a proximal end, which, when the cartridge holder is attached to the outer housing, is inserted into the distal end of the outer housing, wherein the outer housing is provided with a first fixture configured to axially constrain a further component part of the drug delivery device to the outer housing to prevent movement of the further component part in a distal direction, wherein, when the cartridge holder is attached to the outer housing, the proximal end of the cartridge holder axially extends to the first fixture, and/or overlaps with the further component part;
a dose setting element rotatable relative to the outer housing during dose setting and dose dispensing;
a drive member coupled to the dose setting element via a clutch;
a second fixture configured to axially constrain the cartridge holder to the outer housing, wherein the second fixture is located on the inner surface of the outer housing at a position axially distal from the first fixture;
a separate third fixture configured to rotationally constrain the cartridge holder to the outer housing;
a separate fourth fixture configured to axially constrain a cap to the outer housing, wherein the fourth fixture is located on the outer surface of the outer housing at a position axially distal from the first fixture; and a piston rod coupled to the outer housing and to the drive member, wherein the dose setting element is axially constrained to the outer housing by the first fixture of the outer housing.

8. The drug delivery device according to claim 7, wherein the first fixture comprises a groove or bead located on an inner surface of the outer housing and a corresponding bead or groove located on an outer surface of the dose setting element.

9. The drug delivery device according to claim 8, wherein the dose setting element comprises a marked portion extending axially from the bead or groove of the first fixture and which is provided with readable data.

10. The drug delivery device according to claim 7, wherein, when the cartridge holder is attached to the outer housing, at least a portion of the cartridge holder is located radially inwards of the dose setting element and axially overlapping the dose setting element.

11. The drug delivery device according to claim 7, comprising a cartridge containing a medicament.

12. The drug delivery device of claim 11, wherein the medicament comprises a pharmaceutically active compound.

13. The housing according to claim 1, wherein the fourth fixture is located on the outer surface of the outer housing at the axial position of the second fixture.

14. The drug delivery device according to claim 7, wherein the fourth fixture is located on the outer surface of the outer housing at the axial position of the second fixture.

15. A drug delivery device, comprising:

a housing comprising:

an outer housing with a distal end;

a cartridge holder with a proximal end, which, when the cartridge holder is attached to the outer housing, is inserted into the distal end of the outer housing, wherein the outer housing is provided with a first fixture configured to axially constrain a further component part of the drug delivery device to the outer housing, wherein, when the cartridge holder is attached to the outer housing, the proximal end of the cartridge holder axially extends to the first fixture and/or overlaps with the further component part;

a second fixture configured to axially constrain the cartridge holder to the outer housing, wherein the second fixture is located on the inner surface of the outer housing at a position axially distal from the first fixture;

a separate third fixture configured to rotationally constrain the cartridge holder to the outer housing; and a separate fourth fixture configured to axially constrain a cap to the outer housing, wherein the fourth fixture is located on the outer surface of the outer housing at a position axially distal from the first fixture.

16. The drug delivery device according to claim 15, wherein the fourth fixture is located on the outer surface of the outer housing at the axial position of the second fixture.

* * * * *